United States Patent [19]
Dunne et al.

[11] Patent Number: 6,055,867
[45] Date of Patent: May 2, 2000

[54] PANEL TESTING APPARATUS AND METHOD

[75] Inventors: Michael J. Dunne, North Vancouver; Kenneth K. Lau, Vancouver, both of Canada

[73] Assignee: CAE Machinery Ltd., Canada

[21] Appl. No.: 09/296,939

[22] Filed: Apr. 22, 1999

[51] Int. Cl.$^7$ ................................................... G01N 3/32
[52] U.S. Cl. .............................................. 73/849; 73/159
[58] Field of Search .......................... 73/830, 849, 852, 73/159

[56] References Cited

U.S. PATENT DOCUMENTS

| | | |
|---|---|---|
| 2,032,989 | 3/1936 | Kenney et al. . |
| 2,243,842 | 6/1941 | Fearn . |
| 3,158,021 | 11/1964 | Walters et al. . |
| 3,196,672 | 7/1965 | Keller . |
| 4,708,020 | 11/1987 | Lau et al. . |
| 4,722,223 | 2/1988 | Bach et al. . |
| 4,805,679 | 2/1989 | Czinner ................................. 144/357 |
| 4,852,029 | 7/1989 | Pope et al. . |
| 4,932,267 | 6/1990 | Bechtel . |
| 4,991,446 | 2/1991 | Bechtel ................................... 73/849 |
| 5,060,516 | 10/1991 | Lau et al. . |
| 5,074,244 | 12/1991 | Byers . |
| 5,503,024 | 4/1996 | Bechtel et al. . |
| 5,699,274 | 12/1997 | Starostovic, Jr. ....................... 702/113 |
| 5,804,738 | 9/1998 | Bach et al. . |
| 5,892,157 | 4/1999 | Syre ........................................ 73/812 |

*Primary Examiner*—Max Noori
*Attorney, Agent, or Firm*—Townsend and Townsend and Crew LLP

[57] ABSTRACT

Apparatus and method for non-destructively testing the stiffness of wood panels. The apparatus comprises a support framework having infeed, center and outfeed support assemblies mounted to the framework in spaced, successive positions. Each support assembly is adapted to contact the opposed panel surfaces of each panel to define a travel path along which the panel is advanced through the assembly. A first deflection member is provided intermediate the infeed and center support assemblies and is movable to contact one of the panel surfaces as each panel extends between the infeed and the center support assemblies. The first deflection member acts to bend the panel to a first pre-determined curvature. In a similar manner, there is a second deflection member intermediate the center and outfeed support assemblies movable to bend the panel to a second pre-determined curvature. Load cells associated with the first and second deflection members measure the force require to bend the panels to the pre-determined curvatures for calculation of the stiffness of the panels. The infeed, center and outfeed support assemblies are movable relative to each other to position the support assemblies such that the travel paths through the support assemblies define a generally "C" shaped path through the apparatus that accommodates the curvatures that each panel adopts in travelling through the apparatus. The apparatus provides a compact panel testing unit by virtue of the "C" shaped travel path though the apparatus that is able to operate at the high speeds of a production line.

20 Claims, 11 Drawing Sheets

PANEL TESTING APPARATUS AND METHOD

FIELD OF THE INVENTION

This invention relates to a panel testing apparatus and method for non-destructive testing of structural panels for stiffness and strength which finds particular application in testing of composite wood panels or boards.

BACKGROUND OF THE INVENTION

In the production of composite wood panels or boards such as waferboard, plywood, oriented strand board (OSB), particleboard, medium density fibreboard (MDF) and the like, it is desirable to monitor the stiffness and strength of the end product which are typically flat sheets. The stiffness (EI) or the modulus of elasticity (MOE), which can be derived from stiffness, provide an indication of the ultimate strength or modulus of rupture (MOR) of the panel. Since composite wood panels and boards are generally formed on an assembly line, it is also desirable to have testing done at the output end of the assembly line in a testing unit designed for high speed operation.

It is possible to take individual selected panels off the assembly line and subject them to appropriate testing, however, this testing scheme tends to introduce a delay between production and testing and does not lend itself to efficient feedback control for the manufacturing process.

Prior art equipment exists for automatically testing panels or lumber as they exit the production line. This existing equipment generally performs testing by bending of the material. Bending can be done by introducing the panel or lumber into an "S" shaped path. The material is forced to deflect a given amount in its elastic range in two opposite directions and the resultant forces are measured using load cells to determine panel stiffness. The "S" shaped testing method produces an average panel stiffness of both sides of the test panel and assumes a linear stiffness response of the test panel. Examples of prior art testing apparatus and methods that rely on the deflection of the panel or lumber into an "S" shape are U.S. Pat. No. 3,196,672 to Keller and U.S. Pat. No. 4,708,020 to Lau et al.

An alternative to "S" shaped bending of the panel is to subject the panel to bending by applying forces to distort the panel sequentially to two given deflections on the same side of the panel while simply supporting the ends of the panel. This technique can be referred to as "W" shaped bending as the two sequential bending tests, when imagined side by side, distort the panel into a shallow "W" shape. The load to produce each of the given deflections is monitored and the panel stiffness and modulus of elasticity can be determined by the slope of the load-deflection curve. Examples of prior art testing equipment that relies on "W" shaped bending of the panel are U.S. Pat. No. 4,722,223 and U.S. Pat. No. 5,804,738 both to Bach et al. To avoid non-linear regions of the load-deflection curve, two points along the linear region are used to determine the slope rather than relying on one data point and the origin. Preferably, the two data points are determined by applying a first small pre-load of approximately 10% of the ultimate load for the panel, and then applying a final load of approximately 30% of the ultimate load.

Unlike "S" shape bending which measures stiffness based on both sides of the panel, "W" shape bending measures the panel stiffness from one side of the panel corresponding to the intended load bearing side of the panel. Test results indicate that there can be a difference in panel stiffness of up to 6% between opposite sides. Therefore, the "W" shaped bending test is the preferred method for determining the stiffness of load bearing panels.

SUMMARY OF THE INVENTION

Applicant has developed a compact panel stiffness testing apparatus and method that relies on the above described "W" shape bending test. However, to perform the "W" shaped bending test at high speed in order to keep up with production of panels on existing assembly lines, applicant has developed an apparatus and method that directs the panels undergoing testing along an essentially "C" shaped path while conducting the load and deflection measurements of the "W" shaped bending test. The apparatus of the present invention machine can be placed in panel production line so that testing can be done frequently or continuously as the panels are produced with little or no disruption of the assembly line.

Accordingly, in a first aspect the present invention provides apparatus for non-destructively testing the stiffness of panels having opposed panel surfaces and ends comprising:

a support framework;

infeed, centre and outfeed support assemblies mounted to the framework in spaced, successive positions, each support assembly being adapted to contact the opposed panel surfaces of each panel to define a travel path along which the panel is advanced through the assembly;

a first deflection member intermediate the infeed and centre support assemblies movable to contact one of the panel surfaces as each panel extends between the infeed and the centre support assemblies with one end of the panel being supported by the infeed support assembly and the opposite end being supported by the centre support assembly, the first deflection member acting to bend the panel to a first pre-determined curvature;

a second deflection member intermediate the centre and outfeed support assemblies movable to contact the same one of the panel surfaces as each panel extends between the centre and the outfeed support assemblies with one end of the panel being supported by the centre support assembly and the opposite end being supported by the outfeed support assembly, the second deflection member acting to bend the panel to a second pre-determined curvature;

load cells associated with the first and second deflection members to measure the force require to bend the panels to the pre-determined curvatures for calculation of the stiffness of the panels;

whereby the infeed, centre and outfeed support assemblies are movable relative to each other to position the support assemblies such that the travel paths through the support assemblies define a generally "C" shaped path through the apparatus that accommodates the curvatures that each panel adopts in travelling through the apparatus.

In a further aspect, the present invention provides a method for non-destructively testing the stiffness of a panel having first and second panel surfaces comprising:

feeding the panel through first, second and third spaced support assemblies positioned with respect to each other to define a generally "C" shaped path of travel for the panel that accommodates the curvatures that the panel will adopt;

deflecting the panel by a first pre-determined amount by applying a deflecting force to a surface of the panel as the panel passes between the first and second support assemblies with the ends of the panel being supported by the first and second support assemblies;

deflecting the panel by a second pre-determined amount by applying a deflecting force to the same surface of the panel as the panel passes between the second and third support assemblies with the ends of the panel being supported by the second and third support assemblies;

measuring the force required to deflect the panel by the pre-determined amounts; and calculating the stiffness of the panel using the force and deflection data.

The apparatus and method of the present invention permit high speed testing of panels at speeds of up to 600 feet per minute for 5/16 inch thickness panels to match the production speed of state-of-the-art plants.

The panel testing apparatus can accommodate up to ±1/16 inch thickness variation in a panel.

The apparatus tests the panels using the mid-span loading and simply-supported end conditions of the preferred "W" shaped bending test while moving the panels along an essentially "C" shaped path.

BRIEF DESCRIPTION OF THE DRAWINGS

Aspects of the present invention are illustrated, merely by way of example, in the accompanying drawings in which.

DESCRIPTION OF THE PREFERRED EMBODIMENTS

Figure 1:
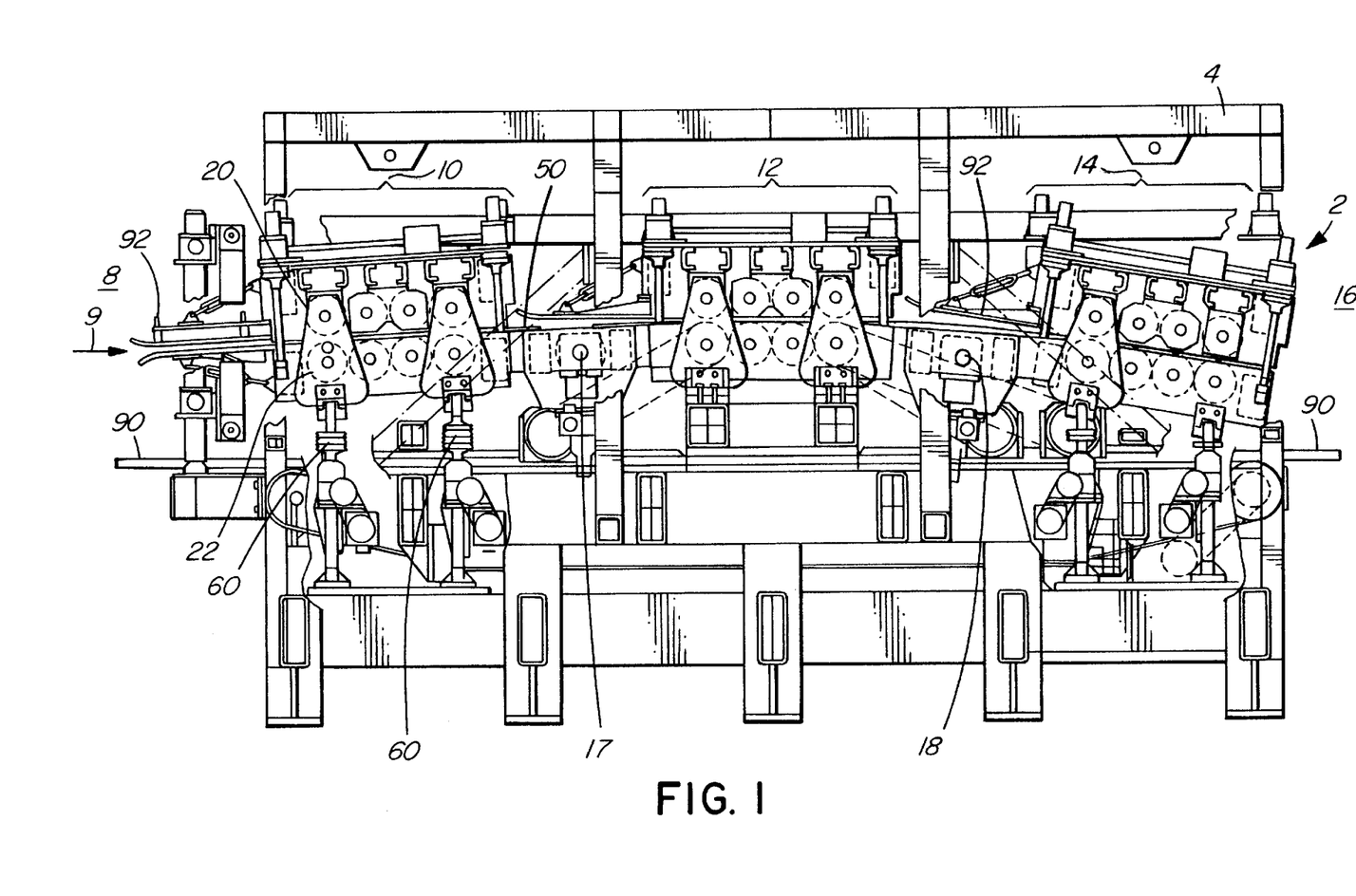
FIG. 1 is a side elevation view of a preferred embodiment of the panel stiffness testing apparatus of the present invention.
Figure 2:
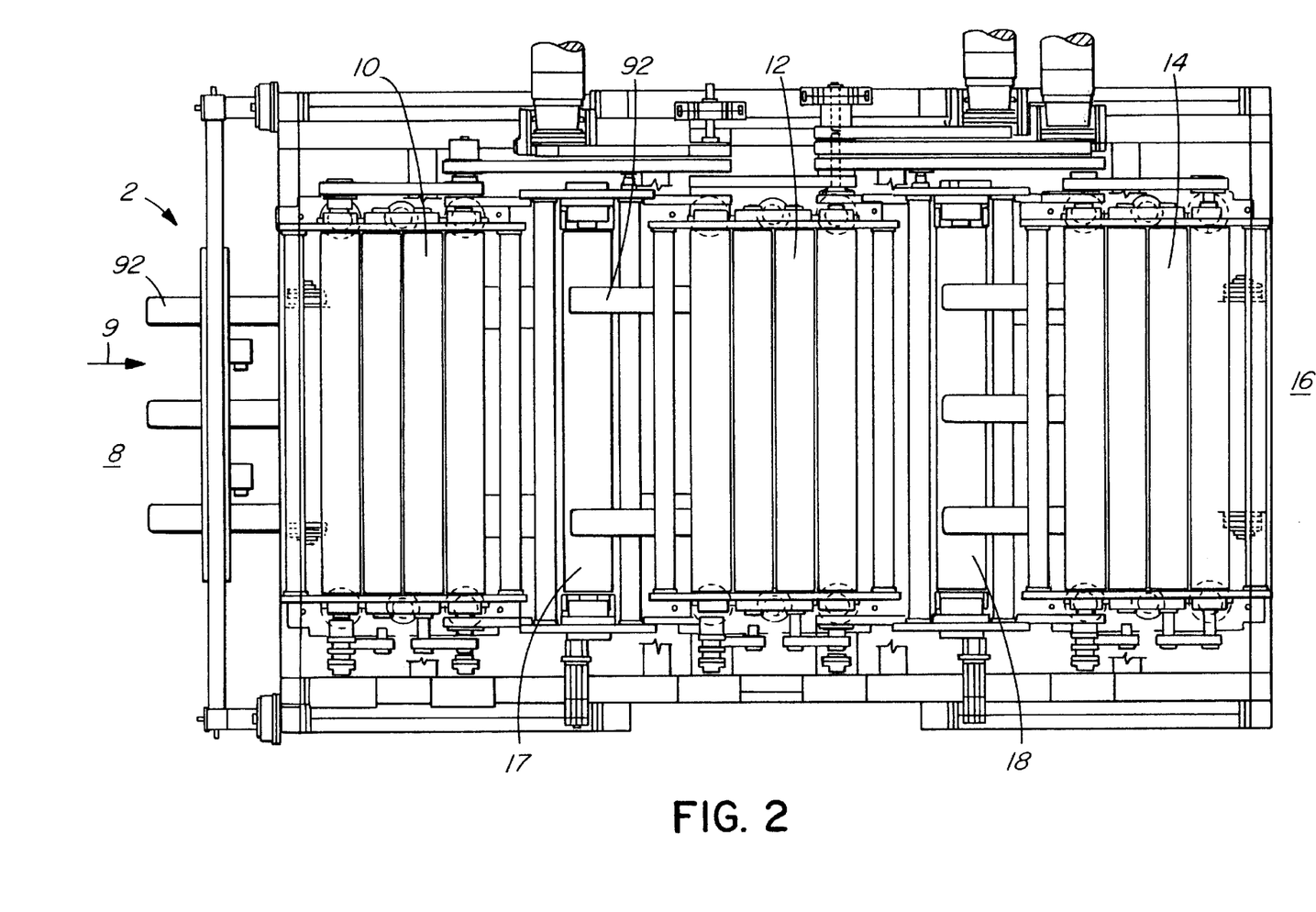
FIG. 2 is a top plan view of the apparatus of FIG. 1.
Figure 3:
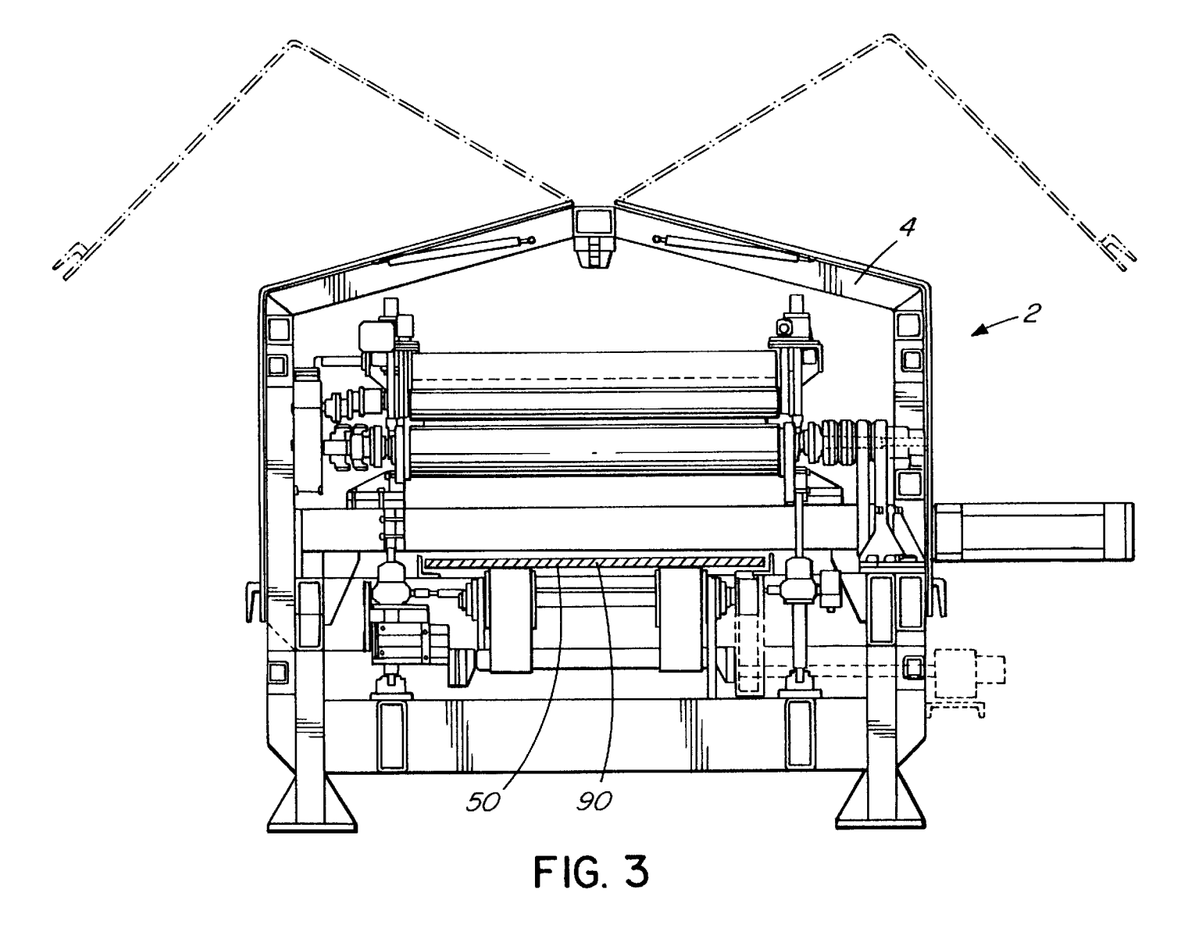
FIG. 3 is an end view of the apparatus of FIG. 1.

Referring to FIGS. 1, 2 and 3, there are shown elevation, plan and end views, respectively, of a preferred embodiment of a non-destructive panel stiffness tester 2 according to the present invention. Tester 2 comprises includes a rigid external support framework 4 which encloses the working components of the apparatus. Support framework 4 is comprised of a series of structural beams selected for their stiffness that are welded together to create a rigid platform. As best shown in FIG. 3, the top half of frame 4 is preferably covered by hinged doors 6 to allow access to the major internal components of the tester for removal, replacement or maintenance.

Referring to FIGS. 1 and 2, panels to be tested are introduced at input end 8 of apparatus 2 to be handled by infeed, centre and outfeed support assemblies 10, 12 and 14, respectively, and discharged from output end 16. The direction of panel flow through the apparatus is indicated by arrow 9 in FIGS. 1 and 2. Panel support assemblies 10, 12, and 14 are mounted to rigid framework 4 in spaced, successive positions. Each support assembly is adapted to contact the opposed surfaces of each panel being tested to define a travel path along which a panel is advanced through the apparatus. Also mounted within framework 4 are deflection members 17 and 18 positioned to apply a deflecting force to a panel as it passes between adjacent panel support assemblies.

Figure 4:
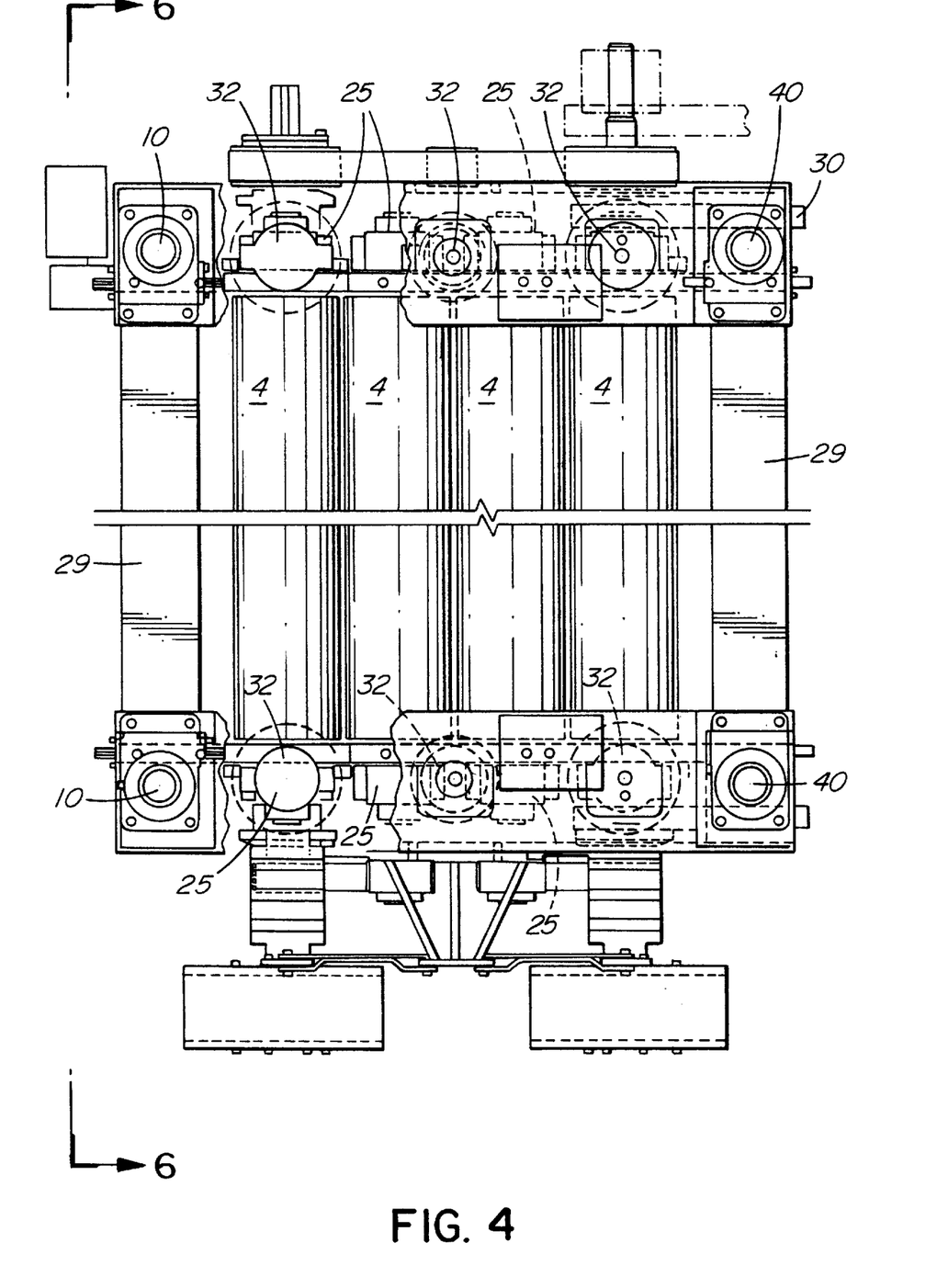
FIG. 4 is a detail plan view of a typical support assembly according to the present invention.
Figure 5:
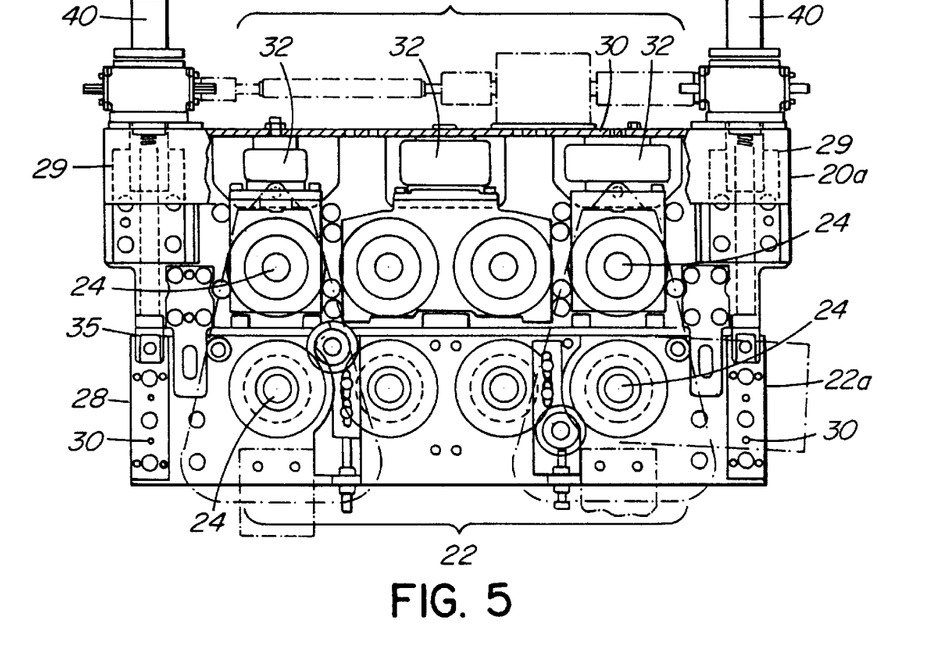
FIG. 5 is a detail elevation view of the support assembly of FIG. 4.
Figure 6:
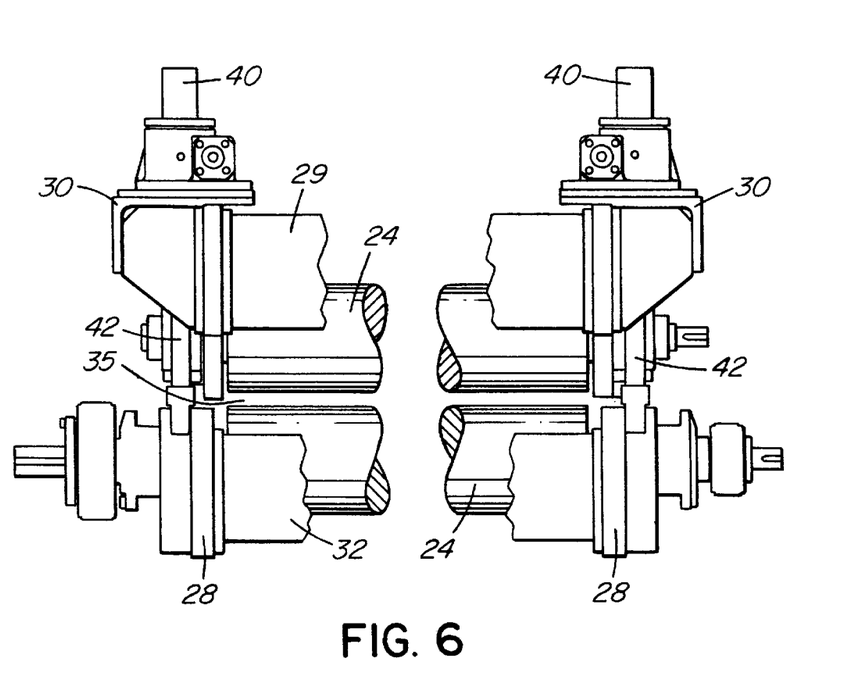
FIG. 6 is a detail view of the screw jack system for adjusting the separation of the upper and lower rolls of the support assembly taken along line 6—6 of FIG. 4.

The panel support assemblies 10, 12 and 14 share a common construction best shown in detail in FIGS. 4, 5 and 6. Each support assembly includes an upper group 20 of four rolls 24 and a lower group 22 of four rolls 24. As shown in FIG. 4, the ends of each roll 24 are rotatably supported by bearing blocks 25. The first and last rolls, or outer rolls, of upper roll group 20 are supported by separate bearing blocks while the two inner rolls are supported by a combined bearing block. Upper beams 30 extend adjacent the upper group 20 of rolls. The ends of each of the upper group 20 of rolls 24 are mounted by bearing blocks 25 to the underside of beam 30 by biasing means in the form of air bags 32. Individual airbags support the ends of each of the outer rolls while the ends of the two inner rolls are each supported by a single airbag. Upper beams 30 are joined by upper cross members 29 to create a generally rectangular upper frame 20a supporting the upper group 20 of rolls. In a similar manner, lower side plates 28 support the bearing blocks 25 that retain the lower group 22 of rolls, and lower cross members 32 join the lower side plates 28 to create a lower frame 22a supporting the lower group 22 of rolls.

The upper and lower groups 20, 22 of rolls are spaced apart to create a gap or nip therebetween that defines the travel path 35 of the panels through each panel support assembly. The lower group of rolls are all driven as are the outer rolls of the upper group, hence the individual bearing blocks and airbags for the upper outer rolls. The driven rolls are powered by a conventional multiple toothed belt drive from an AC synchronous motor through a servo drive (not shown).

The upper and lower groups of rolls act to clamp the panels undergoing testing between the rolls and advance the panel through the assembly. Airbags 32 that support the rolls of upper roll group 20 exert the required clamping force on the panels against the lower group 22 of rolls. Airbags 32 also allow the rolls of upper group 20 to accommodate any local variations in panel thickness. As mentioned previously, the outer rolls of upper group 20 are attached to an individual pair of airbags whereas the inner pair of upper rolls share a pair of airbags. Preferably, the inner pair of upper rolls are loaded to a maximum of 500 pounds nip force to provide the necessary traction on the panel. The outer top rolls, however, will experience the nip forces and the reaction forces from the panel bending between adjacent support assemblies. For example, in the case of the outer top rolls in the centre and outfeed support assemblies, the airbags must be able to withstand a total maximum force of approximately 2000 pounds. The air pressure to the airbags are therefore set at different levels according to the position of the rolls. In addition, airbag pressure is also adjustable to suit different panel thickness settings. Thicker panels develop greater reaction forces as they are deformed and also require higher nip forces. The various air bag pressure settings can be preprogrammed and automatically set when a given panel thickness setting is input.

The roll groups of the infeed and centre support assemblies are equipped with over-running clutches. The drive speeds of the roll groups of all the panel support assemblies are also selected so that each successive group of rolls runs slightly faster (approximately 0.5%) than the preceding group. When a panel passes out of the roll groups in the infeed support assembly and between the roll groups of the centre support assembly, the panel will speed up slightly once it is fully gripped between the rolls of the centre support assembly. The panel is thus caused to move through the infeed support assembly at a higher speed than the driven speed of the infeed groups of rolls. Therefore, the over-running clutch for the infeed support assembly will be over-run so that, in effect, the drive for the infeed groups of rolls are disengaged and the panel is driven solely by the rolls of the centre support assembly. The drag on the panel created by the infeed rolls rotating over the panel surface has been determined to be sufficiently low that only very low tension force are generated in the panel. If necessary, since the drag on the panel should be at a constant, predictable level then compensation can be provided in the calculations of the panel stiffness using data conditioning algorithms.

The process outlined above will be repeated when the panel passes from the centre support assembly to the outfeed support assembly. In this case, the panel will begin to move at the faster speed of the outfeed support assembly and the over-running clutch of the centre support assembly will disengage the drive for the groups of rolls in the centre support assembly.

Prototype testing has shown that slight differences in drive speeds between the roll groups of adjacent support assemblies can have an adverse impact on the load readings for a panel, particularly for thin panels (the thinnest panel being 5/16 inch thick). A difference in drive speeds can put a panel in tension or compression and this creates an error in the load reading. The foregoing over-running clutch system, which effectively disengages the drive of a preceding roll group when driving of the panel is taken up by the subsequent roll group, assures that undesirable compressive and tensile stresses will not be developed.

To accommodate panels of different thicknesses, the spacing of the upper and lower roll groups is adjustable. This is accomplished by virtue of extendable connections in the form of machine screw jacks 40 that reach between the upper and lower frames supporting upper and lower roll groups 20 and 22, respectively. Referring to FIGS. 4 and 6, screw jacks 40 are positioned at the four corners of the upper frame 20a. Screw shafts 42 extend downwardly from each jack body to connect the upper frame 20a to lower frame 22a. The screw jacks 40 are driven together as a group via drive system 44 to set the desired gap between the upper and lower groups of rolls.

Figure 11:
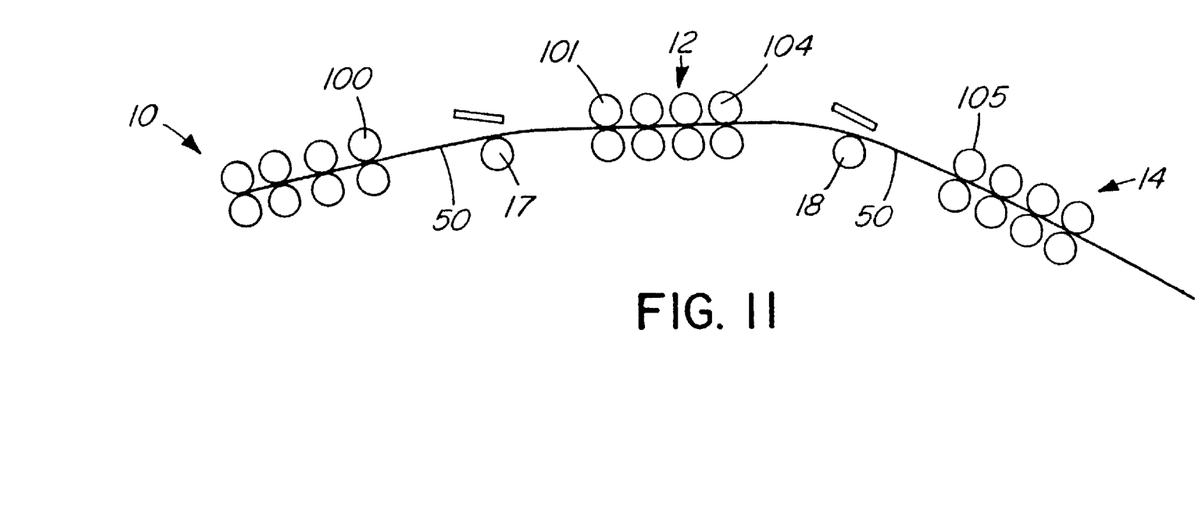
FIG. 11 is a schematic view showing the bending tests conducted by the method and apparatus of the present invention.

The infeed, centre and outfeed support assemblies 10, 12 and 14, respectively, of the apparatus of the present invention are movable with respect to each other to position and align the travel paths 35 of each support assembly to define a generally "C" shaped path that extends through the entire apparatus. Such a path allows the panels being tested to be fed quickly and efficiently through the apparatus. The support assemblies are positioned with respect to each other such that a panel leaving one support assembly is automatically aligned with the subsequent support assembly. FIG. 11 schematically shows the travel path of panels 50 through the roll groups of each support assembly 10, 12 and 14 and past the deflection members 17 and 18 of the panel tester of the present invention.

Referring to FIG. 1, in the illustrated preferred embodiment, relative movement of the various support assemblies is achieved by mounting centre support assembly 12 rigidly to support framework 4 and mounting infeed support assembly 10 and outfeed support assembly 14 to framework 4 for movement. The infeed and outfeed support assemblies are mounted to framework 4 by adjustable mounts to permit variation in the positions of the assemblies to maintain the generally "C" shaped travel path through the apparatus for different thicknesses of panel.

Figure 7:
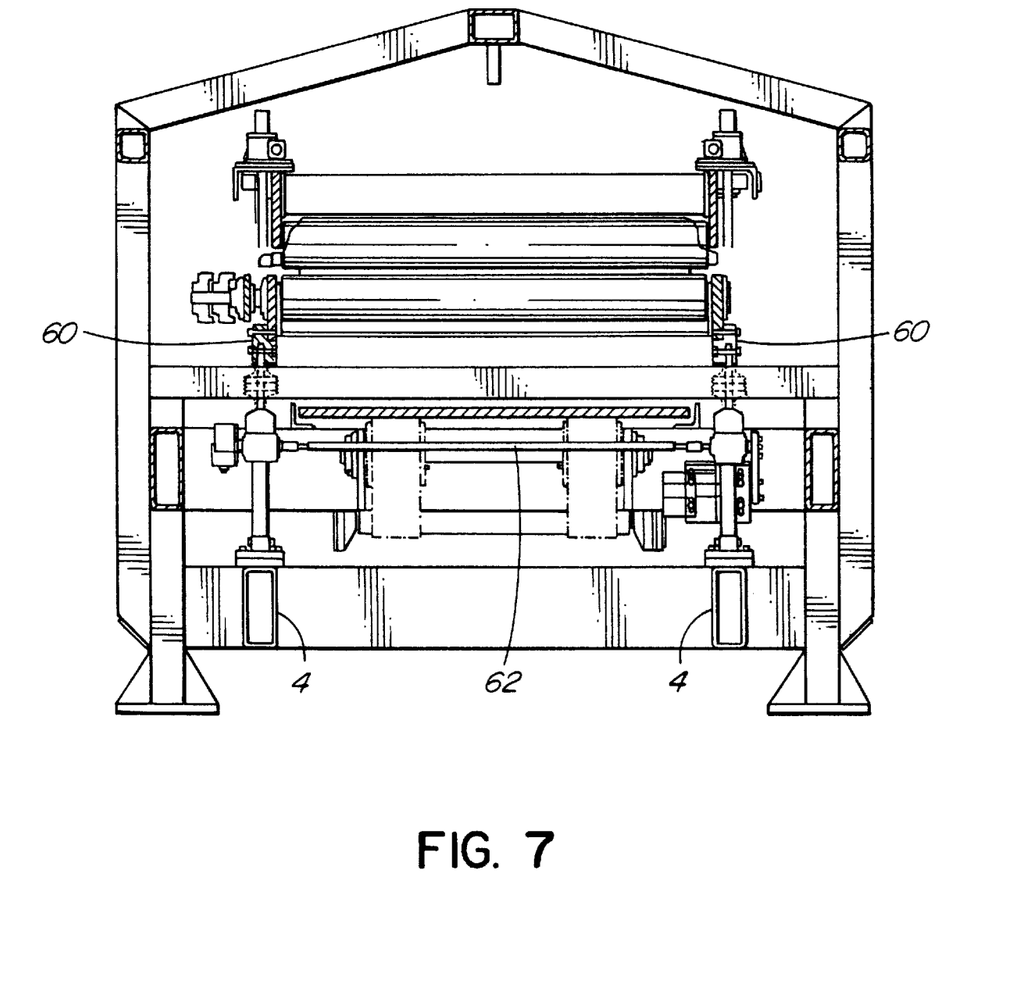
FIG. 7 is detailed end view showing the manner in which the position of the support assemblies is adjusted.
Figure 8:
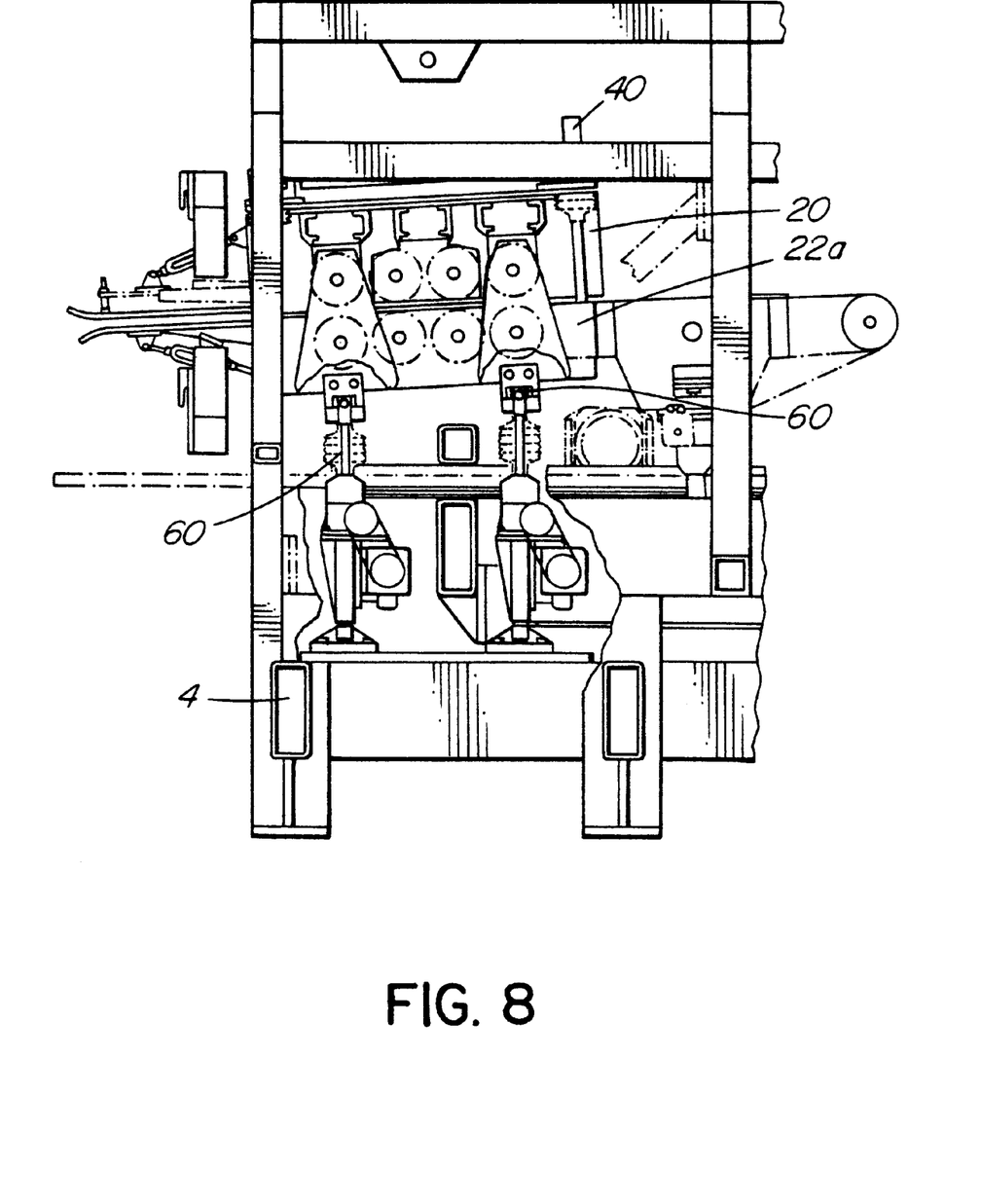
FIG. 8 is a detail elevation view showing the screw jacks used to adjust the position of the support assemblies.

As best shown in FIGS. 7 and 8, the adjustable mounts preferably comprise screw jacks 60 that extend from adjacent the four corners of lower frame 22a of each support assembly to main framework 4. Each screw jack 60 is pivotally mounted at its connection to the lower frame 22a and to framework 4. Screw jacks 60 are coupled together into pairs via drive shafts 62 at the ends of each support assembly 10 and 14 to permit control of the ends of each support assembly. Preferably, jacks 60 are driven by means of computer controlled servo drives to position the infeed and outfeed support assemblies to the correct settings for a particular thickness of panel to ensure a smooth "C" shaped path through the entire apparatus.

Figure 9:
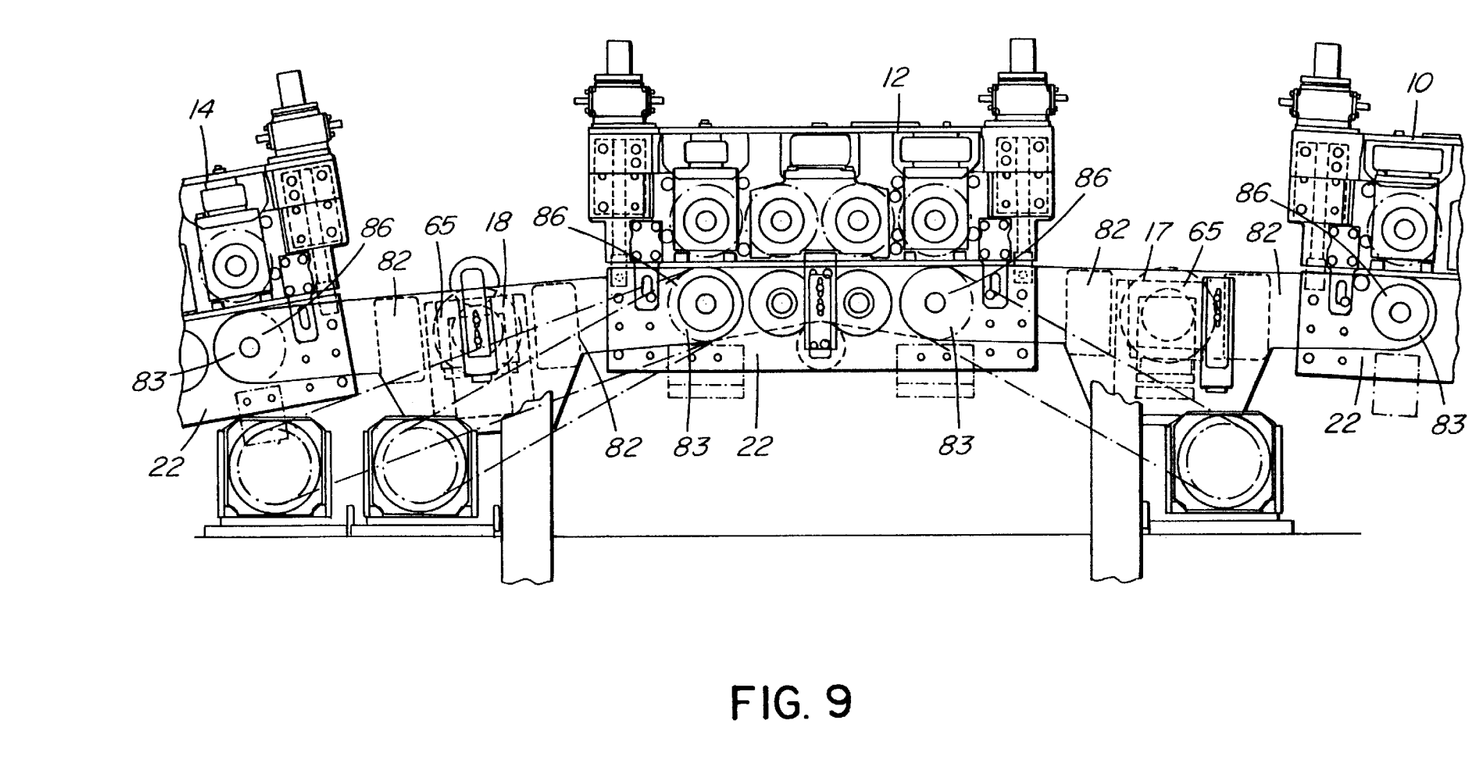
FIG. 9 is a detail elevation view of showing the deflection members of the present invention.
Figure 10:
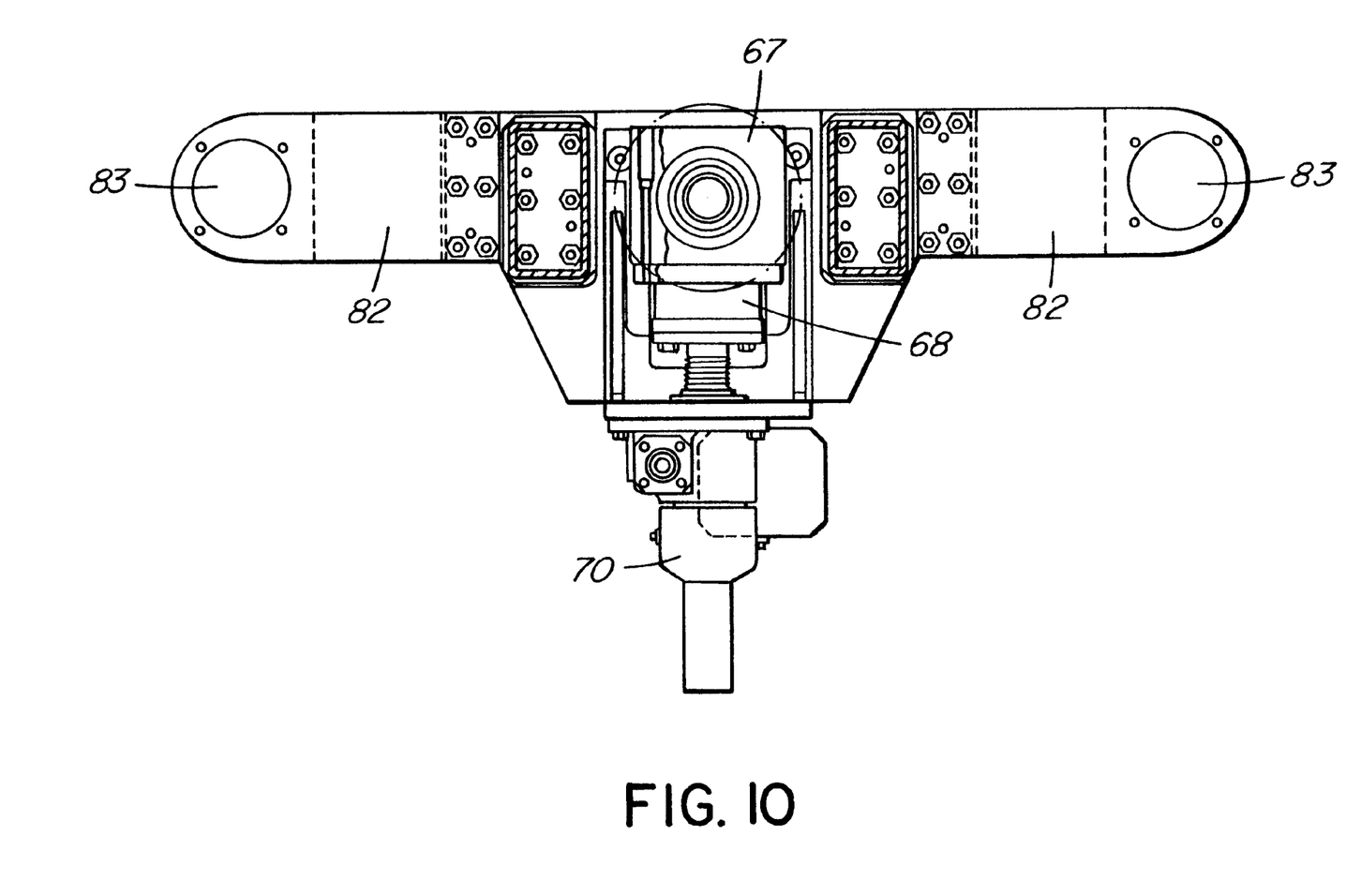
FIG. 10 is a detail elevation view of the link structure associated with the deflection members.
Figure 10A:
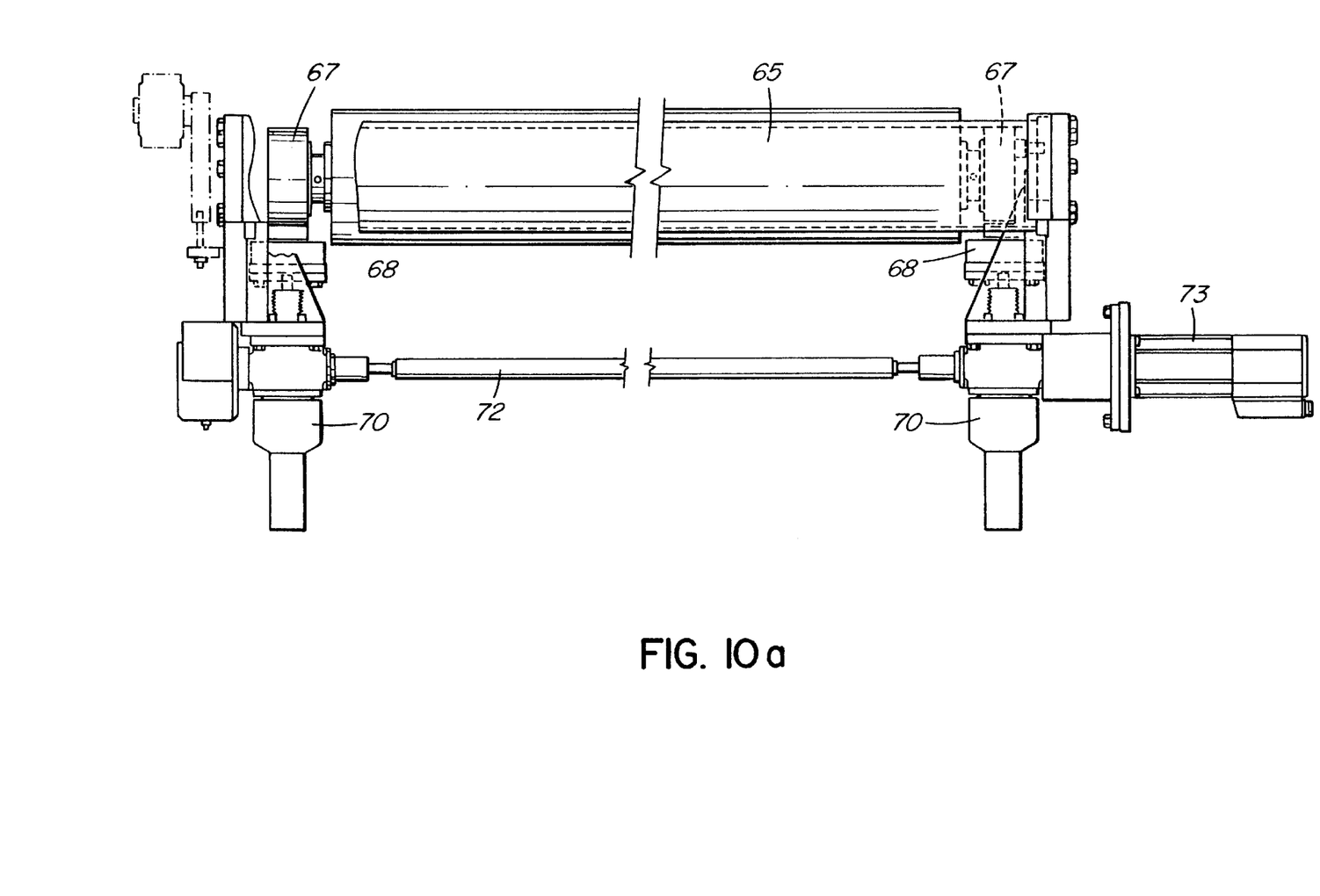
FIG. 10a is a detail end view of a deflection member.

As best shown in FIGS. 9, 10, and 10a, deflection members 17 and 18 are mounted between infeed support assembly 10 and centre support assembly 12, and between centre support assembly 12 and outfeed support assembly 14, respectively. Each deflection member is preferably a roll 65 supported at each end by a bearing block 67 that is in turn mounted atop a load cell 68. Each load cell 68 is mounted to a ball screw jack 70 that is pivotally mounted to support framework 4. As best shown in FIG. 10a, the pair of screw jacks 70 that support the ends of each roll 65 are joined by a drive shaft 72 that is powered by servo motor 73. Motor 73 operates to position deflection roll 65 to contact the lower surface of a panel as the panel travels between the infeed and centre support assemblies (stage 1) or between the centre and outfeed support assemblies (stage 2). The function of deflection rolls 65 is to bend the panel to a pre-determined curvature at each stage and provide a loading point at approximately the centre of each stage with the opposite ends of the panel being supported by the support assemblies between which the panel extends. At the same time, the infeed support assembly and the outfeed support assembly are positioned relative to the centre support assembly such that the travel paths 35 through all the assemblies generally coincide with the generally curved natural path of travel described by a panel of a particular thickness.

The actual load developed at the panel as a result of its bending (up to a maximum of approximately 3000 pounds at stage 2) is measured by load cells 68. Deflection member 18 at stage 2 is preferably positioned to develop a panel curvature that is in the order of three times greater than that at stage 1.

Referring to FIG. 10, each deflection member 17, 18 includes a link structure 80 comprising a pair of arms 82 extending in opposite directions. Arms 82 are mounted to the top of screw jack 70 to move with the jack. Arms 82 of link structure 80 span the distance between the adjacent support assemblies. The ends of arms 82 are formed with apertures 83 that engage about the bearing journals supporting the ends of each of the outer rolls 86 of the lower roll group 22 in each panel support assembly 10, 12 or 14 (FIG. 9). In this manner, link structure 80 serves to connect the support assemblies together so that drive centre distances for the belt driven rolls remain fixed when an adjustment of the position of the infeed or outfeed panel support assemblies is made.

Referring to FIGS. 1 and 3, there is preferably a by-pass conveyor 90 that runs along the entire length of main framework 4 below the panel support assemblies. This conveyor provides an alternative path for the panels 50 through the apparatus while a jam is being cleared from the main travel path through the panel support assemblies or while the apparatus is otherwise not in operation.

The operation of the panel tester of the present invention is maintained and controlled by a computer system that also stores and outputs required panel stiffness data. The operator is required to input the desired panel thickness into the computer to set the apparatus for the correct panel thickness. The computer then sends appropriate positioning commands to the various jacks to set up the machine. Output data from load cells 68 are processed using a series of specially developed algorithms to determine panel stiffness and the panel stiffness data is displayed and/or stored for trending analysis.

In operation, panels to be tested 50 are fed by a conveyor system (not shown) to input end 8 of the apparatus (see FIG. 1). The upper and lower roll groups 20 and 22, respectively, of infeed support assembly 10 clamp and advance the panel along travel path 35 between the roll groups to the centre panel support assembly 12. As the leading edge of the panel 50 emerges from infeed support assembly 10 and is advanced to centre support assembly 12, deflection roll 65 of first deflection member 17 engages the lower surface of the panel. As previously explained, based on the thickness of the panel being tested, the elevation and angle of infeed support assembly 10 are adjusted relative to the centre support assembly 12 to feed panel 50 along a path that substantially coincides with the natural panel curvature between the assemblies and the leading edge of the panel is advanced smoothly and guided to be received between the upper and lower roll groups of centre support assembly 12. To facilitate the efficient movement of the panels between adjacent support assemblies, guide arms 92 extend forwardly from each support assembly (FIG. 1 and 2) to assist in guiding the leading edge of each panel.

The purpose of the panel testing apparatus of the present invention is to replicate the simply supported panel deflection test conditions of the previously discussed "W" shaped bending test at high speed and in a compact space. As illustrated schematically in FIG. 11, this is achieved in the following manner: once panel 50 extends between infeed support assembly 10 and centre support assembly 12, the panel is effectively simply supported at both ends by rolls 100 and 101 with the remaining rolls of the support assemblies supporting and isolating the panel weight and any vibration. The roll of deflection member 17 acts to deform panel 50 to a pre-determined induced curvature and load cells associated with the deflection member record the load experienced by the panel. In a similar manner, panel 50 is then advanced from centre support assembly 12 to outfeed support assembly 14. Deflection member 18 is positioned to exert a greater pre-determined curvature to panel 50 than in stage 1 and outfeed support assembly 14 is positioned in the path of the leading edge of the panel. Rolls 104 and 105 effectively simply support the ends of the panel and the load cells associated with deflection member 18 record the load that the panel is subject to.

The panel testing apparatus of the present invention is designed to test panel thicknesses in the range between 5/16 inch to 1¼ inches. Ideally, the position of the infeed and outfeed support assemblies would be set according to the actual panel thickness. For practical reasons, this is not possible and the panel thicknesses are therefore preferably grouped into eight thickness groups of ⅛ inch increments. The apparatus tests all panel thicknesses within a given thickness group using the same apparatus settings relating to the gap between roll groups and the elevation and angle of the infeed and outfeed support assemblies. For a given thickness group, the apparatus is set to accommodate the simply supported conditions of the mean thickness panel for the group. As a result, an error exists for all other thicknesses within the group. The thickness group for 5/16 inch to 7/16 inch thick panels are most sensitive to this error because of the relatively low deflection force readings for these thinner panels. Finite Element Analysis (FEA) has been performed to assess the magnitude of the error for the worst case of a 5/16 inch thick panel. The results of the analysis indicate that by using the theoretical span and deflection for a given thickness in each thickness group to calculate panel stiffness, the error due to imperfect set up conditions of the apparatus is insignificant, that is, a maximum error of about 0.01% in load readings. Therefore, the positioning of the infeed and outfeed support assemblies for groups of panel thicknesses at increments of ⅛ inch between groups does not adversely affect the stiffness measurements generated by the apparatus of the present invention.

Figure 12:
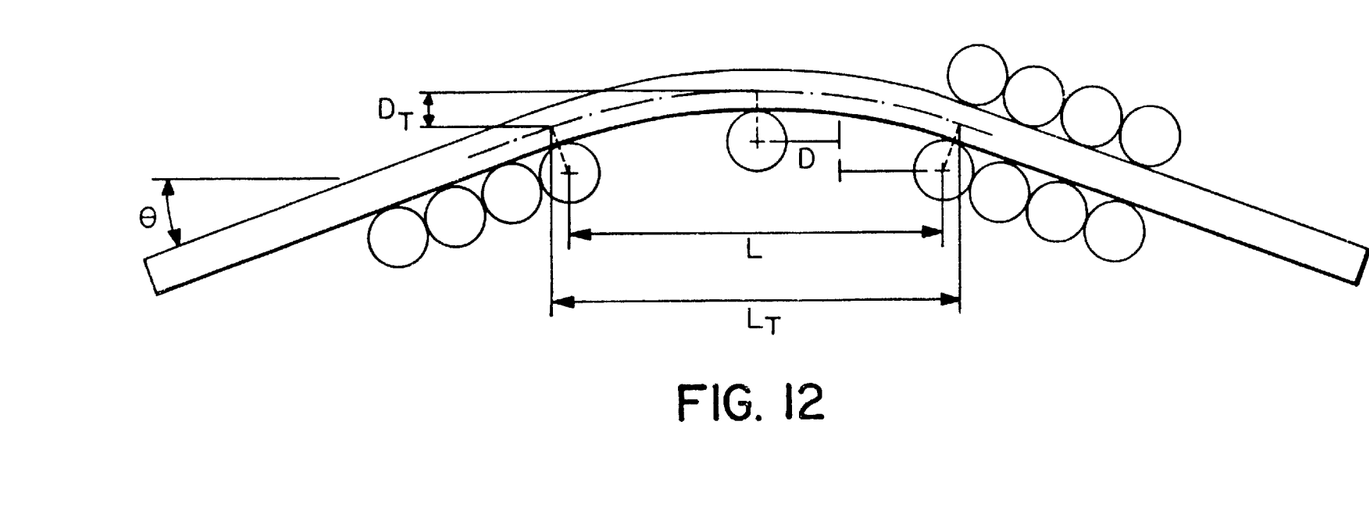
FIG. 12 is a schematic view showing the deflection of a panel in the apparatus of the present invention.

Based on prototype testing, applicant has developed a general formula to calculate stiffness based on the measurements acquired by the apparatus of the present invention according to equation 1 as follows:

$$\text{Stiffness} = EI = (\text{Load} * \text{Span}^3)/(48 * \text{Deflection}) \quad (1)$$

where
Load=the measured deflection force
Span=L=the distance between the supported ends of the panel
Deflection=D=the distance the deflection roll is moved to establish the pre-determined curvature of the panel The above parameters are shown in FIG. 12 which is a schematic view showing the deflection of a panel between adjacent stages of the apparatus of the present invention. It will be noted that the machine span L and machine deflection D are not the same as the true span $L_T$ and the true deflection $D_T$. It is desirable to use the true span and deflection to obtain the most accurate stiffness readings.

Examples of machine settings for stages 1 and 2 of the apparatus of the present invention are as follows:

| Thickness Group | Mean Panel Thickness | Stage 1 Deflection (inch) | Stage 2 Deflection (inch) | Stage 1 Theta degrees | Stage 2 Theta degrees |
| --- | --- | --- | --- | --- | --- |
| 1 | ⅜" | 0.35 | 1.00 | 1.6685 | 4.7470 |
| 2 | ½" | 0.25 | 0.75 | 1.1925 | 3.5670 |
| 3 | ⅝" | 0.20 | 0.60 | 0.9540 | 2.8560 |
| 4 | ¾" | 0.16 | 0.50 | 0.7635 | 2.3815 |
| 5 | ⅞" | 0.14 | 0.42 | 0.6680 | 2.0015 |
| 6 | 1" | 0.12 | 0.37 | 0.5725 | 1.7635 |
| 7 | 1⅛" | 0.11 | 0.33 | 0.5250 | 1.5730 |
| 8 | 1 7/32" | 0.10 | 0.30 | 0.4775 | 1.4305 |

For a given panel thickness, the true deflection and span can be computed using equations 2 and 3 as follows:

$$\text{True Deflection} = D_T = D + [R + T/2) - (R + T/2)\cos(\text{Theta})] \quad (2)$$

$$\text{True Span} = L_T = L + (2R + T)\sin(\text{Theta}) \quad (3)$$

where D is the machine deflection in inches

L is the machine span in inches=36"

R is the roll radius in inches=2.865"

T is the nominal panel thickness in inches

Theta is the angle indicated in FIG. 12

Equation 4 below can be used for computing the panel stiffness of a specific panel location. Equation 5 can be used for computing the average stiffness of a panel.

$$\text{Panel Stiffness} = EI = [(P_2 * L_{T2}^3) - (P_1 * L_{T1}^3)]/[48 * (D_{T2} - D_{T1})] \quad (4)$$

where $P_1$ is the measured force at stage 1 for a specific panel location $P_2$ is the measured force at stage 2 for the same location as $P_1$ $L_{T1}$ is the true span of stage 1

$L_{T2}$ is the true span of stage 1

$D_{T1}$ is the true deflection of stage 1

$D_{T2}$ is the true deflection of stage 1

$$\text{Average Panel Stiffness} = [\text{SUM}(EI_i)_{(i=1 \text{ to } n)}]/n \quad (5)$$

where $EI_i$ is the panel stiffness for location i as per equation (4)

n is the number of panel locations

As indicated above in formula (4), the panel stiffness is determined based on the difference of the load readings between stages 2 and 1 for the same panel location. Preferably, the computer control system is set to sample load data at both stage 1 and stage 2 at 25 points along the center five feet length of an eight foot panel.

The various panel support assemblies of the present invention have been designed to provide decoupling between the stage 1 and stage 2 deformation testing of the apparatus of the present invention. The panel support assemblies also provide decoupling between the testing stages and the outside world. This ensures that there is no interaction between the operation of one testing stage with another. This also ensures that anything happening to the panels as they enter or leave the panel tester will not effect the stiffness measurements. It has been determined by using Finite Element Analysis (FEA) that four pairs of rolls are preferably employed in each roll group of the support assemblies to provide the decoupling described above. A further benefit of the support assembly design of the present invention is vibration isolation between each support assembly so that impulses resulting from a panel edge entering the first pair of rolls in a support assembly are not detected by the load cells in the next stage. It has been determined that use of a low pass filter to cut out noise above 5 hertz will provide better and more accurate load measurements. This is based on prototype test results indicating that the frequency of panel stiffness variability does not exceed 5 hertz within a panel along its length. The natural frequencies of OSB panels were measured and determined to be in the range of 7.65 hertz to 14.75 hertz for 3/8 inch to 1 1/8 inch thick panels, respectively, under mid-point loading of a simply supported span of 44 inches. The natural frequencies of OSB panels for a span of 36 inches, as is the case with the panel testing apparatus of the present invention, and constrained under the boundary conditions of the apparatus can be expected to be higher and are estimated to be in the range of 10 to 20 hertz. The natural frequency of the apparatus was designed to be relatively high (35 hertz and above) so that use of a low pass filter is able to isolate the measurement frequency domain from any panel or machine natural vibration frequencies.

The computer control system of the apparatus of the present invention has also been designed to recover gracefully from a panel jam within the panel support assemblies. In the event of a jam, the computer activates jacks 60 supporting the infeed 10 and outfeed 14 panel support assemblies to fully extend the jacks so that these support assemblies are positioned horizontally and in-line with fixed centre support assembly 12. Jacks 70 associated with deflection members 17 and 18 are retracted to drop rolls 65 to their lowest position so that the rolls are in the same plane or lower than the lower roll groups 22 in the support assemblies. Jacks 40 positioned between the upper 20 and lower 22 roll groups are then fully extended so that the space between the roll groups is maximized. Any panel jammed in the apparatus will then be completely free of any constraints and can be withdrawn by hand.

Although the present invention has been described in some detail by way of example for purposes of clarity and understanding, it will be apparent that certain changes and modifications may be practised within the scope of the appended claims.

What is claimed is:

1. Apparatus for non-destructively testing the stiffness of panels having opposed panel surfaces and ends comprising:

a support framework;

infeed, centre and outfeed support assemblies mounted to the framework in spaced, successive positions, each support assembly being adapted to contact the opposed panel surfaces of each panel to define a travel path along which the panel is advanced through the assembly;

a first deflection member intermediate the infeed and centre support assemblies movable to contact one of the panel surfaces as each panel extends between the infeed and the centre support assemblies with one end of the panel being supported by the infeed support assembly and the opposite end being supported by the centre support assembly, the first deflection member acting to bend the panel to a first pre-determined curvature;

a second deflection member intermediate the centre and outfeed support assemblies movable to contact the same one of the panel surfaces as each panel extends between the centre and the outfeed support assemblies with one end of the panel being supported by the centre support assembly and the opposite end being supported by the outfeed support assembly, the second deflection member acting to bend the panel to a second pre-determined curvature;

load cells associated with the first and second deflection members to measure the force require to bend the panels to the pre-determined curvatures for calculation of the stiffness of the panels;

whereby the infeed, centre and outfeed support assemblies are movable relative to each other to position the support assemblies such that the travel paths through the support assemblies define a generally "C" shaped path through the apparatus that accommodates the curvatures that each panel adopts in travelling through the apparatus.

2. Apparatus as claimed in claim 1 in which each of the infeed, centre and outfeed support assemblies comprises:

an assembly frame; and an upper group of rotatable rolls and a lower group of rotatable rolls mounted to the assembly frame, the upper and lower groups of rollers having a space therebetween to define the travel path of the panels through the assembly with the upper and lower groups of rolls acting to clamp and advance the panels through the assembly.

3. Apparatus as claimed in claim 2 in which the lower group of rolls is driven to advance the panels through the support assembly.

4. Apparatus as claimed in claim 3 in which the outer rolls of the upper group of rolls are driven.

5. Apparatus as claimed in claim 3 in which the drive speed of the rolls is set such that each group of rolls runs faster than the preceding group.

6. Apparatus as claimed in claim 2 in which the stiffness of the panel is calculated according to the general formula:

$$\text{Stiffness}=EI=(\text{Load}*\text{Span}^3)/(48*\text{Deflection})$$

where

Load=the force required to bend the panels to the pre-determined curvatures

Span=L=the distance between the supported ends of the panel when extending between one of the infeed and outfeed support assemblies and the centre support assembly;

Deflection=D=the distance the deflection members move to bend the panel to the pre-determined curvature.

7. Apparatus as claimed in claim 2 in which each of the upper and lower groups of rolls has four rolls.

8. Apparatus as claimed in claim 2 in which the upper and lower groups of rolls of each support assembly are adapted to be movable with respect to each other for adjustment of the space therebetween to accommodate panels of different thicknesses.

9. Apparatus as claimed in claim 8 in which the upper group of rolls are mounted to an upper roll frame and the lower group of rolls are mounted to a lower roll frame and the upper and lower roll frames are connected via extendable connections.

10. Apparatus as claimed in claim 9 in which the extendable connections comprise machine screw jacks.

11. Apparatus as claimed in claim 9 in which the upper group of rolls are mounted to the upper roll frame by biasing means to bias the upper rolls against the panel and the lower rolls.

12. Apparatus as claimed in claim 11 in which the biasing means are airbags.

13. Apparatus as claimed in claim 2 in which the centre support assembly is rigidly mounted to the support framework and the infeed and outfeed support assemblies are mounted to the support framework by adjustable mounts to permit adjustment of the positions of the infeed and outfeed support assemblies to maintain the generally "C" shaped travel path through the apparatus for different thicknesses of panel.

14. Apparatus as claimed in claim 13 in which the adjustable mounts comprise screw jacks extending between the assembly frames and the main support framework.

15. Apparatus as claimed in claim 2 in which the each of the first and second deflection members comprises a roll with opposite ends of the roll mounted to the load cells.

16. Apparatus as claimed in claim 15 including a link structure to which the load cells are mounted, the link structure extending between adjacent support assemblies to maintain the distances between the support assemblies when the position of support assemblies with respect to each other is adjusted.

17. Apparatus as claimed in claim 16 in which the link structure extends between the end rolls of the lower group of rolls.

18. Apparatus as claimed in claim 15 in which each roll is mounted to the framework by extendable connections to permit movement of the roll to engage the one side of the panel.

19. Apparatus as claimed in claim 1 including a by-pass conveyor in the support framework to provide an alternative path to pass panels without stiffness testing.

20. A method for non-destructively testing the stiffness of a panel having first and second panel surfaces comprising:

feeding the panel through first, second and third spaced support assemblies which are movable with respect to each other to define a generally "C" shaped path of travel for the panel that accommodates the curvatures that the panel will adopt;

deflecting the panel by a first pre-determined amount by applying a deflecting force to a surface of the panel as the panel passes between the first and second support assemblies with the ends of the panel being supported by the first and second support assemblies;

deflecting the panel by a second pre-determined amount by applying a deflecting force to the same surface of the panel as the panel passes between the second and third support assemblies with the ends of the panel being supported by the second and third support assemblies;

measuring the force required to deflect the panel by the pre-determined amounts; and calculating the stiffness of the panel using the force and deflection data.

* * * * *